United States Patent
Gibbs-Davis et al.

(10) Patent No.: US 9,193,993 B1
(45) Date of Patent: Nov. 24, 2015

(54) NUCLEIC ACID AMPLIFICATION BY A DESTABILIZATION METHOD

(71) Applicants: Julianne M Gibbs-Davis, Edmonton (CA); Rosalie Dawn McKay, Sherwoodpark (CA); Yimeng Li, Beijing (CN); Jade Lam, Calgary (CA); Abu Kausar, Dhaka (BD); Catherine Jennifer Mitran, Edmonton (CA)

(72) Inventors: Julianne M Gibbs-Davis, Edmonton (CA); Rosalie Dawn McKay, Sherwoodpark (CA); Yimeng Li, Beijing (CN); Jade Lam, Calgary (CA); Abu Kausar, Dhaka (BD); Catherine Jennifer Mitran, Edmonton (CA)

(73) Assignee: Julianne M. Gibbs-Davis (CA)

( * ) Notice: Subject to any disclaimer, the term of this patent is extended or adjusted under 35 U.S.C. 154(b) by 57 days.

(21) Appl. No.: 13/789,657

(22) Filed: Mar. 7, 2013

Related U.S. Application Data

(60) Provisional application No. 61/607,827, filed on Mar. 7, 2012.

(51) Int. Cl.
*C12P 19/34* (2006.01)
*C12Q 1/68* (2006.01)

(52) U.S. Cl.
CPC .............. *C12Q 1/6844* (2013.01); *C12P 19/34* (2013.01)

(58) Field of Classification Search
CPC ........................................ C12P 19/34
USPC ....................................... 435/91.2
See application file for complete search history.

(56) References Cited

U.S. PATENT DOCUMENTS

| | | | |
|---|---|---|---|
| 5,516,663 A * | 5/1996 | Backman et al. ............ | 435/91.2 |
| 6,361,944 B1 * | 3/2002 | Mirkin et al. ................ | 435/6.11 |
| 6,509,383 B1 * | 1/2003 | Fisher et al. .................... | 521/32 |
| 7,943,348 B2 * | 5/2011 | Cho et al. ..................... | 435/91.2 |
| 2012/0288857 A1 * | 11/2012 | Livak .......................... | 435/6.11 |

* cited by examiner

*Primary Examiner* — Ardin Marschel
(74) *Attorney, Agent, or Firm* — Invention To Patent Services; Alex Hobson

(57) ABSTRACT

The invention is directed to a method for isothermally amplifying a DNA sequence involving hybridizing a destabilizing DNA template to complementary nucleotide fragments to form a first nicked duplex; ligating the first nicked duplex to form a product duplex comprising the DNA sequence and the template, wherein the product duplex is capable of dissociating to release the DNA sequence and the template; and repeating these steps to generate multiple copies of the template and the DNA sequence. Further, the method may also involve hybridizing the DNA sequence to complementary destabilizing fragments or probes to form a second nicked duplex; ligating the second nicked duplex to form the product duplex comprising the DNA sequence and the template, wherein the product duplex dissociates to release the DNA sequence and the template; and repeating these steps to generate multiple copies of the template and the DNA sequence.

25 Claims, 11 Drawing Sheets

NUCLEIC ACID AMPLIFICATION BY A DESTABILIZATION METHOD

CROSS REFERENCE TO RELATED APPLICATIONS

This application claims priority from U.S. Provisional Patent Application No. 61/607,827, filed on Mar. 7, 2012, entitled ISOTHERMAL DNA AMPLIFICATION, incorporated herein by reference in its entirety.

FIELD OF THE INVENTION

The invention relates to methods for amplifying a DNA sequence using a destabilizing DNA template.

BACKGROUND OF THE INVENTION

DNA-based systems have been developed that are capable of performing sophisticated functions initiated by molecular recognition. Key examples are the DNA walkers where directional motion or load pick-up, transfer, and release are achieved with molecular and spatial selectivity (Gu et al., 2010; Lund et al., 2010). However, attempts to develop autonomous DNA self-replicating systems without specific sequence requirements have in recent years lagged behind (Lincoln, 2009; Patzke et al., 2007; Ye et al., 2000; Zielinkski et al., 1987). As one of the hallmarks of organisms is their ability to amplify information and materials through biocatalysis and self-replication, the development of truly biomimetic systems capable of integrated functions requires incorporating amplification into self-assembly and nanotechnology (Aldaye et al., 2008; Patzke et al., 2007; Paul et al., 2004). Replicating DNA systems not only provide tools for DNA-based nanotechnology and insights into the origins of life, but also can be used to isothermally amplify signal in DNA detection, which can simplify the requirements for point-of-care diagnostics (Aldaye et al., 2008; Connolly et al., 2010; Orgel, 1992; Patzke et al., 2007; Paul et al., 2004).

One method for introducing amplification into DNA-based systems involves generating turnover in DNA-templated processes (Grossman et al., 2008). To achieve turnover, the DNA template that facilitates the reaction of two complementary fragment strands (FIG. 1, steps A-B) must dissociate from the product after it has formed (FIG. 1, step C). However, for ligation reactions, turnover is minimal under isothermal conditions owing to the enhanced affinity of the template for the ligated product (Grossman et al., 2008). Many detection strategies have thus focused on template-triggered scission and transfer reactions rather than ligations to avoid this product inhibition (Grossman et al., 2008). One strategy for introducing turnover into ligation reactions exploits the sensitivity of DNA to destabilizing modifications present in the middle of a duplex (Silverman et al., 2006; Ye et al., 2000; Zhan et al., 1997). By ligating strands at a destabilizing site, the stability of the hybridization complex can be modified without changing the temperature or any other reaction condition (Li et al., 2003). If the stabilities of the complexes before and after ligation are properly balanced, isothermal turnover should be achieved.

SUMMARY OF THE INVENTION

The present invention relates to methods for isothermally amplifying a target DNA sequence using a cross catalytic cycle whereby a destabilizing DNA template is generated in situ from destabilizing DNA probes and the target sequence copies are generated from another set of probes. In one aspect, the invention comprises a method for isothermally amplifying a DNA sequence of interest (target sequence), comprising the steps of:

(a) preparing target probes complementary to the target sequence wherein at least one probe comprises a destabilizing moiety;

(b) allowing the target probes to hybridize to the target sequence and ligating the target probes together to form a first product duplex comprising the target sequence and a newly generated destabilizing template;

(c) allowing the first product duplex to dissociate to release the target sequence and the destabilizing template; and (d) preparing template probes complementary to the destabilizing template sequence that when ligated together form the original target sequence;

(e) allowing the probes to hybridize to the destabilizing template and ligating the template probes together to form a second product duplex comprising a newly generated target sequence and a destabilizing template;

(f) allowing the second product duplex to dissociate to release the target sequence and the destabilizing template; and (g) repeating steps (a) to (f) to generate multiple copies of the target sequence and the destabilizing template.

In one embodiment, the probe destabilizing moiety comprises an abasic or model abasic, butyl, cis-butenyl, or ethyl group. In one embodiment, the probes comprise one or more mismatches which are preferably spaced away from the ligation site.

In one embodiment, the method comprises the further step of detecting the target sequence or the destabilizing template. The detection step may comprise the steps of fluorescently labeling the probes and detecting fluorescence after electrophoretic separation. Alternatively, the probes may be separately labeled with a fluorescent donor and a fluorescent acceptor, which when ligated together produce detectable Forster resonant energy transfer. In a further alternative embodiment, one probe may be immobilized to a surface while another probe is labeled with a gold nanoparticle, which is covalently bound to the surface following ligation of the two probes. The gold nanoparticle may then be detected by catalytic silver reduction plating.

In one embodiment, ligation is conducted at a temperature ranging between about 13° C. to about 30° C. In one embodiment, ligation is conducted using a T4 DNA ligase. In one embodiment, the concentration of the ligase ranges from about 1 to about about 5 units of enzyme per reaction. In one embodiment, the equivalents of template ranges from about 0.001 to about 0.01.

The isothermal amplification of DNA may be used to detect target sequences to detect and identify genomic DNA, or to detect gene mutations, including single point mutations.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the an from this detailed description.

BRIEF DESCRIPTION OF THE DRAWINGS

The invention will now be described by way of an exemplary embodiment with reference to the accompanying simplified, diagrammatic, not-to-scale drawings.

DETAILED DESCRIPTION OF EMBODIMENTS

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

To facilitate understanding of the invention, the following definitions are provided.

"Amplification" means the production of multiple copies of a DNA sequence.

A "complementary sequence" is a sequence of nucleotides which forms a duplex with another sequence of nucleotides according to Watson-Crick base pairing rules where "A" pairs with "T" and "C" pairs with "G."

"Destabilizing" means the ability of templates, fragments or probes to impart a destabilizing site to a duplex such that its component strands dissociate more readily, typically but not necessarily without the need to vary any reaction condition.

A "duplex" means at least two polynucleotides that are fully or partially complementary undergo Watson-Crick type base pairing among all or most of their nucleotides so that a complex is formed.

"Hybridization" is used to mean the formation of a duplex.

"Isothermal" means a process which takes place at a substantially constant temperature.

"Ligating" means forming a covalent bond or linkage between the termini of two or more nucleic acids, e.g. polynucleotides, in a template-driven reaction. The nature of the bond or linkage may vary. As used herein, ligation may be carried out enzymatically.

"Mismatch" means a base pair between any two of the bases A, T (or U for RNA), G, and C other than the Watson-Crick base pairs G-C and A-T. Possible mismatches include, but are not limited to A-A, T-T (or U-U), G-G, C-C, T-G (or U-G), C-A, T-C (or U-C), and A-G.

"Nicked duplex" means a duplex having a single-stranded cut or break.

"Nucleic acid" means polynucleotides such as deoxyribonucleic acid (DNA), and, where appropriate, ribonucleic acid (RNA). The term should also be understood to include, as equivalents, analogs of either RNA or DNA.

A "polynucleotide" is a linear sequence of ribonucleotides (RNA) or deoxyribonucleotides (DNA) in which the 3' carbon of the pentose sugar of one nucleotide is linked to the 5' carbon of the pentose sugar of another nucleotide. The deoxyribonucleotide bases are abbreviated as "A" deoxyadenine; "C" deoxycytidine; "G" deoxyguanine; "T" deoxythymidine; "I" deoxyinosine. Some oligonucleotides described herein are produced synthetically and contain different deoxyribonucleotides occupying the same position in the sequence. The blends of deoxyribonucleotides are abbreviated as "W" A or T; "Y" C or T; "H" A, C or T; "K" G or T; "D" A, G or T; "B" C, G or T; "N" A, C, G or T.

Figure 2:
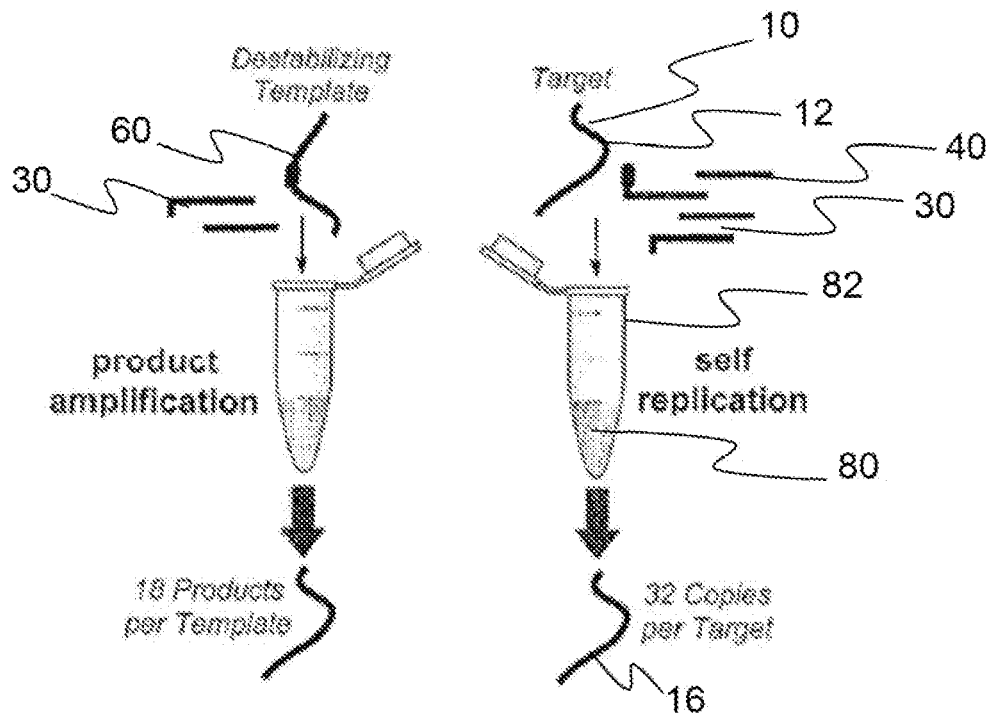
FIG. 2 is a schematic diagram comparing the product/copy yield of amplification using the destabilizing template (left) and self-replication using a cross-catalytic cycle (right).

The present invention relates to methods for isothermally amplifying a DNA sequence using destabilizing DNA probes which are ligated to form a destabilizing template. Introducing destabilizing modifications into a DNA template leads to turnover in a DNA-templated ligation reaction. Utilizing destabilizing DNA template, the product duplex is destabilized after ligation and releases the DNA template which is free to template further ligation reactions. Introducing turnover into simple, enzymatic ligation reactions provides an avenue for amplifying DNA-based assemblies constructed by enzymatic ligation. Isothermal ligation strategies also have potential applications in cross-catalytic replication of DNA, which represents a general method for amplifying any DNA sequence. By incorporating a cross-catalytic cycle, the present invention also achieves self-replication (FIG. 2).

In one embodiment, the invention comprises a method for isothermally amplifying a DNA sequence of interest (target sequence), comprising the steps of:

(a) preparing probes complementary to the target sequence wherein at least one probe comprises a destabilizing moiety;

(b) allowing the probes to hybridize to the target sequence and ligating the probes together to form a first product duplex comprising the target sequence and a newly generated destabilizing template;

(c) allowing the first product duplex to dissociate to release the target sequence and the destabilizing template; and (d) preparing probes complementary to the destabilizing template sequence that when ligated together form the original target sequence;

(e) allowing the probes to hybridize to the destabilizing template and ligating the probes together to form a second product duplex comprising a newly generated target sequence and a destabilizing template;

(f) allowing the second product duplex to dissociate to release the target sequence and the destabilizing template; and (g) repeating steps (a) to (f) to generate multiple copies of the target sequence and the destabilizing template.

The following is a specific example of one embodiment of the present invention. This example is offered by way of illustration and is not intended to limit the invention in any manner.

Figure 3:
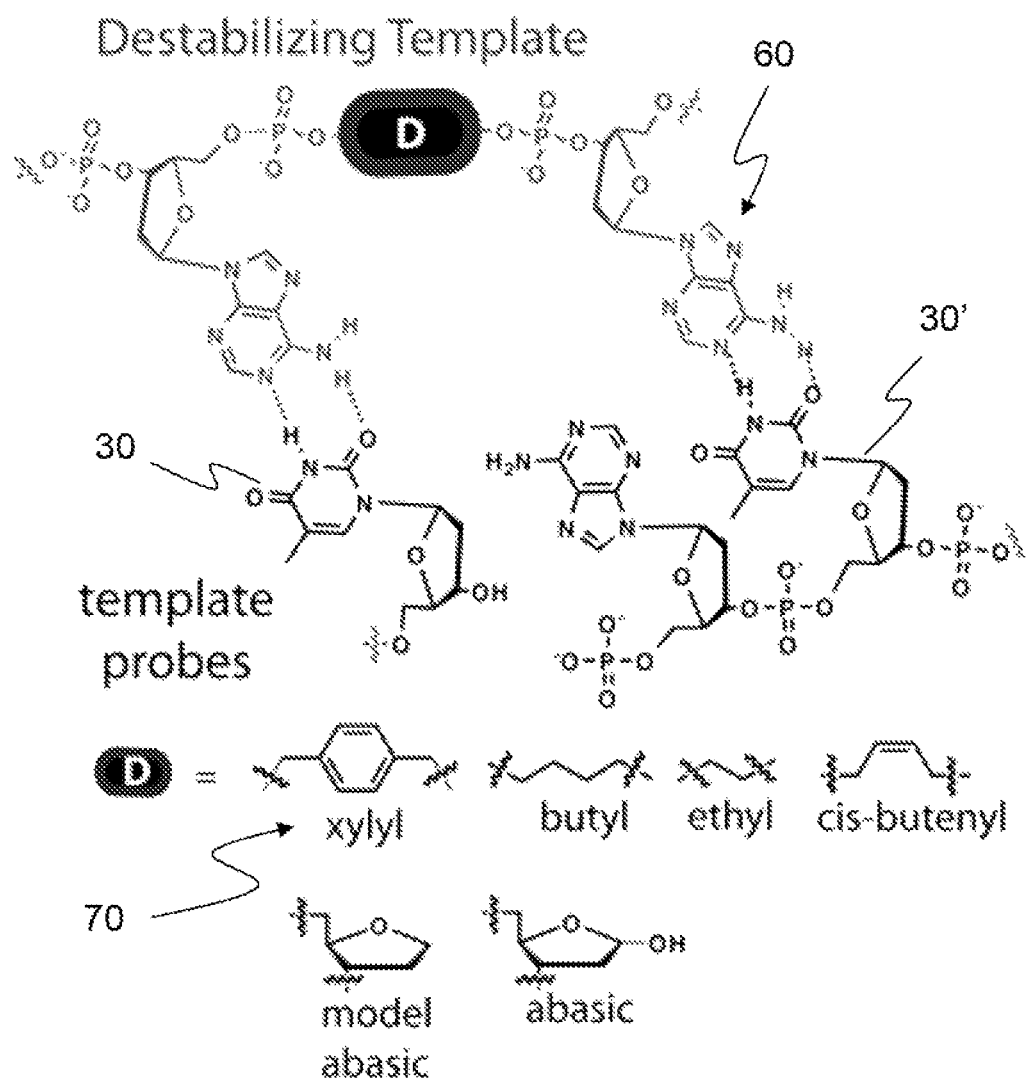
FIG. 3 is a schematic diagram showing the nicked site prior to ligation. The destabilizing templates contain a modification (D) in place of a thymidine. The perfect template contains the complementary thymidine (T).

Isothermal turnover in nonenzymatic, chemical ligation systems has been useful in DNA and mRNA detection. Destabilization may be introduced in a ligating fragment strand by adding an alkyl group between the terminal nucleotide and the electrophilic end (Abe et al., 2004). After ligation with a nucleophilic fragment using target DNA as a template, the resulting alkyl bridge causes the product duplex to dissociate. The present invention involves creating a DNA template containing a destabilizing moiety, such as a short alkyl chain, in place of a complementary nucleotide (FIG. 3). A model abasic DNA lesion ("Ab") known to destabilize DNA duplexes was also investigated (FIG. 3) (Matray et al., 1998). PNA analogues of abasic groups have been demonstrated by Grossman et al. (2008) to avoid product inhibition and improve selectivity in chemical ligation systems using PNA (Dose et al., 2006; Ficht et al., 2005). In the present invention, the model abasic group results in a template that is missing a base but still contains the canonical phosphate-sugar backbone.

Figure 1:
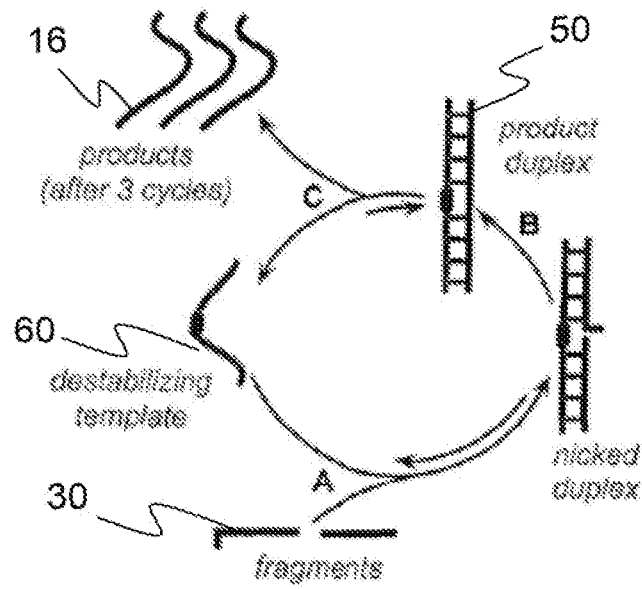
FIG. 1 is a schematic diagram showing isothermal turnover in DNA-templated ligation reactions using a destabilizing DNA template.

Achieving sufficient turnover requires that the product duplex be less stable than the nicked duplex (FIG. 1). However, because of multivalency, the product duplex is invariably more stable, even with the destabilizing modification (Mammen et al., 1998). A more reasonable goal is to introduce a modification that renders the product and nicked duplexes closer in stability, so that a temperature can be found where both can form but remain labile. To determine whether the duplex stabilities of the destabilizing templates were optimal, their thermal dissociation behavior was monitored. The temperature at which half the duplex has dissociated is the melting temperature (Tm), providing a way to compare duplex stabilities.

Figure 4:
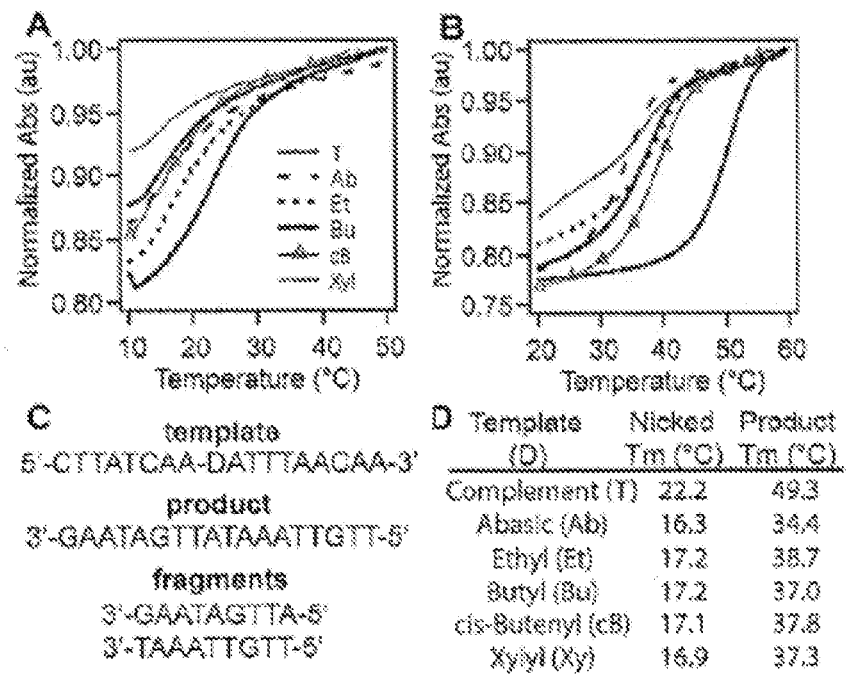
FIGS. 4A-B show the thermal dissociation profiles of nicked duplexes (template:fragments) (FIG. 4A) and product duplexes (template:product) (FIG. 4B) with [DNA]=1.3 μM per strand (pH 7.0, 10 mM PBS, 10 mM $MgCl_2$).
FIG. 4C shows the sequences of strands where D is thymidine or a destabilizing group.
FIG. 4D is a table of dissociation (melting) temperatures (Tm).

FIGS. 4A and B show the thermal dissociation curves for the nicked duplexes (template+two fragments) and the product duplexes (template+product), respectively. The 18-base sequence and the position of the nicked site and destabilizing group are provided in FIG. 4C. To illustrate the extent of destabilization, these results were compared with the behavior of a perfectly complementary system (FIGS. 4A and B, black solid traces, where D=thymidine). For all of the destabilizing templates, the decrease in Tm between the nicked and corresponding product duplexes was 18-22° C. In contrast, the Tm difference was 27° C. for the natural DNA system (FIG. 4D). The smaller ΔTm for the destabilized templates suggested that a temperature might be found where hybridization of the nicked duplex (FIG. 1, step A) and dissociation of the product duplex (FIG. 1, step C) were both possible.

Figure 5:
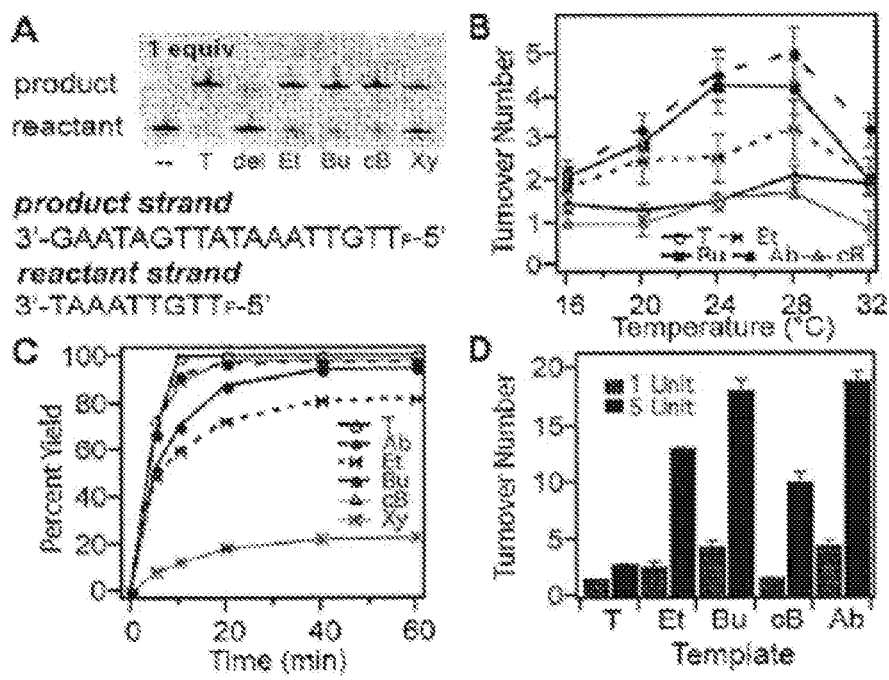
FIG. 5A shows fluorescent images of denaturing polyacrylamide gels for ligation mixtures using fluorescein-labelled thymine ($T_F$) with one equivalent template.
FIG. 5B is a graph showing turnover number (TON) versus temperature for ligations with 0.01 equivalents of template.
FIG. 5C is a graph showing percent yield versus time with one equivalent template.
FIG. 5D is a graph showing TON versus enzyme concentration (1 unit vs 5 unit) with 0.01 equivalent template at 24° C. (Template Labels: —no template; T thymidine; del deletion; Et ethyl; Bu butyl; cB cis-butenyl; Xy xylyl; Ab abasic. Conditions unless noted: 1 equiv (1.4 μM) $T_F$-labeled reactant, 1 Unit T4 DNA ligase, 20 h, 16° C.).

In ligation experiments, the template was mixed with the complementary reactive strands (containing a 3'-OH and 5'-phosphate at the ligation site) and 1 unit of T4 DNA ligase for each 15-µL reaction. One unit is the amount of enzyme needed to catalyze the conversion of 1 nmol of 32P-labeled pyrophosphate into ATP in 20 min at 37° C. The 5' end of one of the fragments was labelled with fluorescein to follow ligation via fluorescent imaging after separation by denaturing polyacrylamide gel electrophoresis. The gel image in FIG. 5A illustrates the ligation mixtures with one equivalent of template after 20 hours of reaction time, where a product band was evident for all of the destabilizing templates. This result indicates that T4 DNA ligase tolerates unnatural modifications to the DNA template near the site of ligation. Ligation with all of the destabilizing templates was hampered when the ligation site was opposite the 3' end rather than the 5' end of the destabilizing group.

To determine whether these destabilizing templates could turn over in the reaction, the ligation reaction was monitored with substoichiometric amounts of template. At 20° C., when 0.01 equivalents of complementary template (T) were used, only 1.3% of the fluorescent fragment strand was ligated, indicating that the dissociation of the product duplex was unfavorable. In contrast, using the same amount of an abasic template (Ab) led to 3.2% of the ligated product. From the ratio of [product]/[template] the turnover number (TON) was calculated. The amount of turnover for the perfect template (T) was between 1 to 2 for all reaction temperatures using 0.01 equivalents of template (FIG. 5B). In contrast, the turnover was greater than two for several of the destabilizing templates. The only inactive templates that yielded little or no ligated product under these substoichiometric conditions were the xylyl template (Xy) and a template containing a deletion of the thymidine (del, data not shown). With the cis-butenyl template, turnovers were between 0.9 and 1.7, which indicated that this rigid linkage did not promote catalytic behavior.

For all of the active destabilizing templates, the highest TON was observed at 28° C., well above the melting temperature of their corresponding nicked duplexes (FIG. 5B). The highest TON observed at this enzyme concentration was 5.0 for the abasic template (Ab). Without being bound by theory, the decrease in nicked duplex stability at 28° C. may be compensated for by the faster rate of ligation or dissociation of the product duplex. However, at temperatures higher than 28° C., the decrease in TON suggests that the formation of the nicked duplex becomes unfavorable. At all temperatures, no background ligation was observed in the absence of template (FIG. 5A). The enzyme requirement that the DNA be double-stranded eliminated any background reaction illustrating a major advantage to this method. In one embodiment, a catalyst may be employed which favors double-stranded DNA, as a method of avoiding non-templated background in chemical ligations (Ye et al., 2000).

To determine how the destabilizing template influenced the rate of ligation, the yield versus time was measured in ligations using one equivalent of template. Within ten minutes ligation is complete when natural DNA template (T) is used (FIG. 5C). The rate of ligation for perfect template should first be measured to verify the enzyme activity. If the enzyme is less active due to improper storage or handling, no turnover is observed. Most of the destabilizing templates are only a little slower with the Ab and cB template requiring 20 minutes, and the other templates requiring less than 40 minutes. Without being bound by theory, the leveling off of the signal for the ethyl and butyl templates may be attributed to subtle differences in the extinction coefficients used to calculate the DNA concentration. The leveling off of the xylyl suggests that most of the xylyl template is in a conformation that does not allow for hybridization or ligation. Comparing these results with those of chemical ligation methods which demonstrate slower rates of ligation indicates that faster ligation methods lead to greater turnover (Abe et al., 2004; Sando et al., 2004; Dose et al., 2006; Ficht et al., 2005).

The typical ligase concentration for ligating nicked duplexes was 1 unit enzyme per equivalent of fluorescent fragment strand (1.4 µM, 15 µL). To determine whether increasing enzyme concentration would increase the amount of turnover, ligation reactions using concentrated enzyme (5 units per reaction) were performed with the same amount of template (0.01 equivalents). At higher enzyme concentration, the DNA template (T) still exhibited a TON close to one. In contrast, the Bu and Ab templates generated 18 product strands per template (FIG. 5D), which is 5-fold higher than the maximum turnover number of 3.5 previously reported by Grossman et al. (2008) using similar probe (1.2 µM) and template (12 nM) concentrations (Dose et al., 2006).

Figure 6:
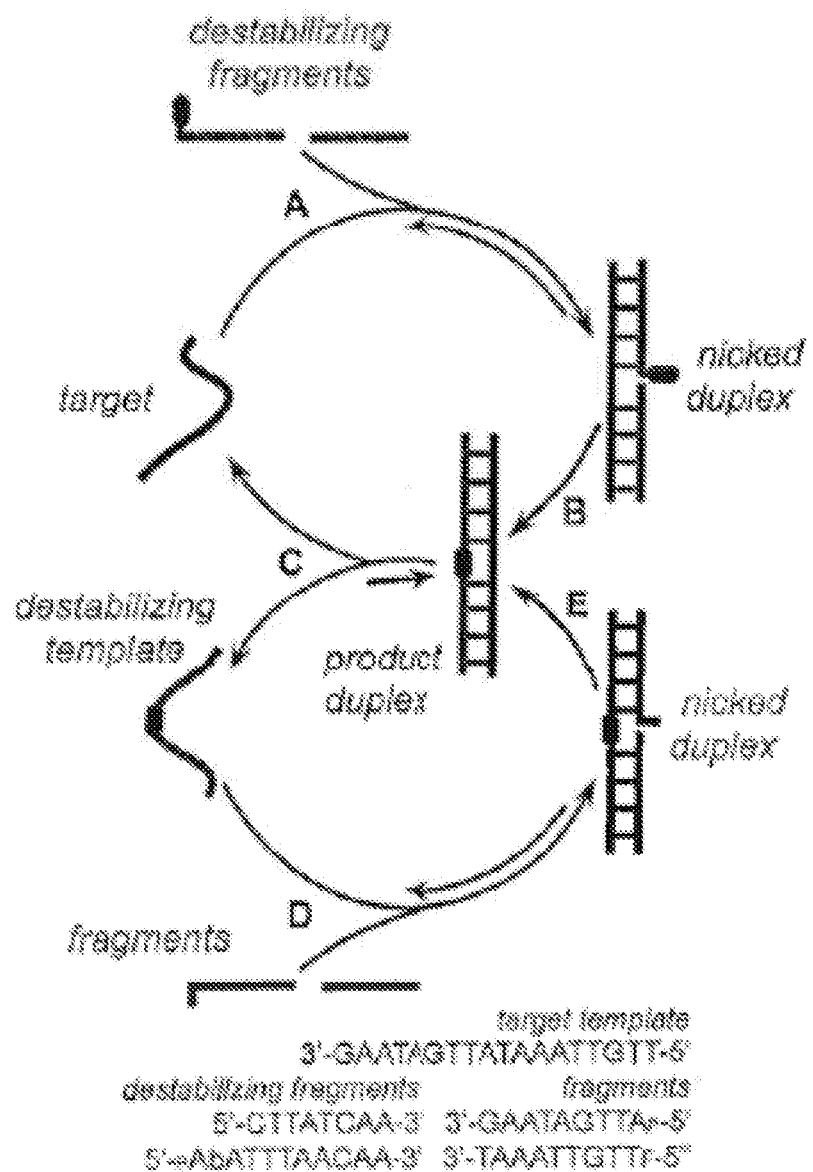
FIG. 6 is a schematic diagram showing cross catalytic cycles using destabilizing fragments.

Embodiments of the present invention may be applied in smart, DNA-based systems; for example, an environmental stimulus can be used to release destabilizing template causing the amplification of a DNA material, for example, DNA-ligated gold nanoparticle aggregates (Claridge et al., 2008). In a method for native DNA detection, another complementary ligation cycle must be included. A cross-catalytic replication strategy may be initiated by a native DNA strand representing a target sequence (FIG. 6). The destabilizing template is formed in situ from destabilizing probes by a ligation reaction templated by the natural DNA target (FIG. 6, steps A and B). As a result of ligation, the same product duplex is formed as in the previous cycle. Consequently, the product:template duplex is destabilized, leading to the release of the original target and a newly formed destabilizing template (FIG. 6, step C). This destabilizing template can now generate a copy of the original target template, which goes on to catalyze the formation of more destabilizing templates (FIG. 6, steps D-E). As the product of each cycle is a template for the other, amplification of the original target mayensue.

Figure 7:
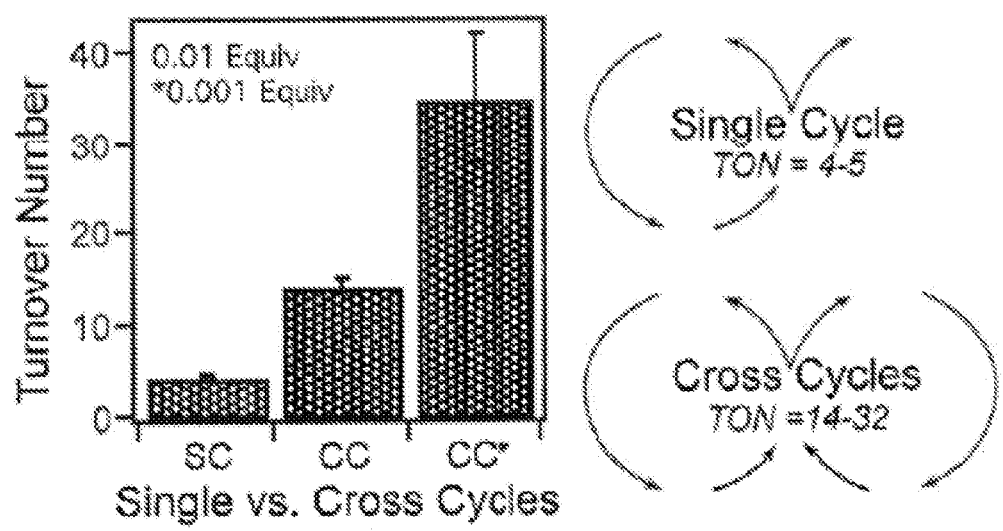
FIG. 7 is a graph comparing the turnover numbers for a single catalyst cycle using a model abasic destabilizing template and fragments (SC), and a cross catalytic cycle using target as template and fragments, one of which contained an abasic group (CC) (Conditions: 0.01 equiv template (14 nM); *0.001 equiv (1.4 nM); 1 Unit T4 DNA ligase; 24° C.; 20 h).

To experimentally verify that cross catalysis occurs, the fragment strands listed in FIG. 6 were combined, including a fluorescent modified fragment corresponding to the bottom cycle ($T_P$, fluorescein-modified thymine). A target DNA sequence was introduced which, although active in the top cycle, should have no effect on the fluorescein-labeled fragment; thus, the formation of any fluorescent ligated product would signify cross catalysis. T4 DNA ligase ligates a destabilizing probe terminated with a 5'-phosphate model abasic (Ab) group (Verly et al., 1983). Target-initiated cross catalysis occurred for the Ab-substituted system (FIG. 7). Self-replication was observed in this two cycle system, and the exhibited cross-catalytic TON was greater than that for the single catalytic cycle (TON 14 vs 4.5; CC vs SC, respectively). Decreasing the number of equivalents of template (CC*) further increased the number of cross-catalytic turnovers, indicating that dissociation is favored as the fragment:template ratio becomes larger (Abe et al., 2004; Dose et al., 2006). The highest cross-catalytic turnover of 32 corresponds to the target undergoing on average 32 cycles of self-replication (FIG. 7, CC*).

For the cross-catalytic reactions using 1 unit of ligase and the 5' phosphate model abasic destabilizing probe, a small level of background was observed (0.5% and 3.7% product at 20 and 24° C., respectively, with no template present). The more concentrated enzyme (5 units per 15 µL reaction), capable of ligating blunt ends, displayed very high background under identical reaction conditions. In contrast, the 5'-phosphate thymidine fragment exhibited a large amount of background (25% ligation product at 20° C.). Without restriction to a theory, it is believed the reason for the high background in the natural system is based on the probe design, which leads to a one-base overhang of thymidine on one fragment and deoxyadenosine on the other. Although this overhang exists in the Ab-modified system, replacing the thymidine with the model abasic group prevents hydrogen bonding with the adenine, thus minimizing nonspecific joining of the fragments. Consequently, very little background ligation is observed.

In one embodiment, target probes are made complementary to the target sequence (FIG. 8), at least a portion of which probes comprise a destabilizing moiety. Upon mixing the probes and the target, the probes hybridize to the target. T4 DNA ligase ligates the two probes together to form a destabilizing template, as long as one of the two probes comprises a destabilizing moiety. This template is generated in situ and is not initially present in the ligation mixture. As a result of the destabilizing group, the target and destabilizing template dissociate, releasing both strands to template more reactions. While the released target continues to template the formation of the destabilizing template, each new destabilizing template that forms and is released hybridizes to a set of template probes (complementary to the destabilizing template) that are present and causes them to ligate. This new strand formed from the ligation of two template probes, is identical or substantially similar to the initial target sequence. Every cross-catalytic cycle thus yields a new target sequence, which can then participate in making more destabilizing template and consequently more target. Such cross-catalytic cycles are essential for achieving exponential amplification of the target sequence, similar to PCR. Eventually some probes become ligated in the absence of the target. This background reaction is observed but it requires longer reaction times than target-initiated reactions.

In an alternative embodiment, the method starts with the synthesis of a destabilizing template from target probes, which then turns a copy of the target sequence, which may then be used in the cross-catalytic cycle described above.

Figure 9A:
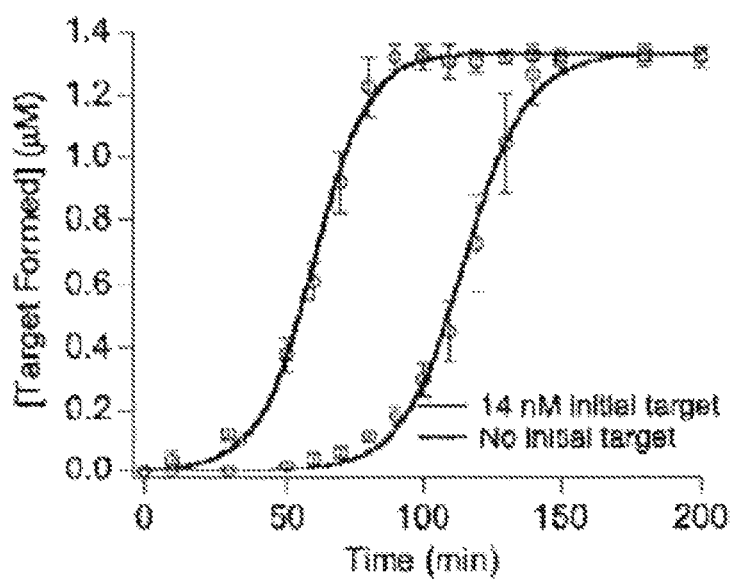
FIGS. 9A-B are graphs showing the measured target formed over time (FIG. 9A) and the difference in target formed over time for 14 nM initial target and no initial target (FIG. 9B).
Figure 9B:
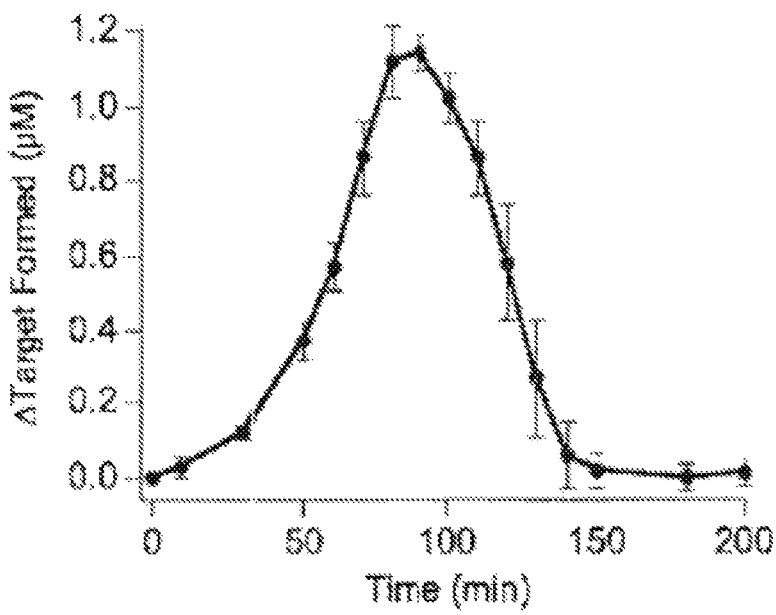

By subtracting the yield of a control reaction lacking initial target from a target-initiated replication, target DNA can be detected from the difference in target formed (Measured Target Formed, FIG. 9A; ΔTarget Formed, FIG. 9B). Multiple sequences may thus be detected, indicating that this destabilization approach is very general. Moreover, the present invention enables detection of single mismatches and genomic DNA from cell lysate, and achieves fM detection limits. Use of a high concentration of T4 DNA ligase can lead to very rapid amplification. Consequently, thousands of turnovers within hours may be observed.

In one embodiment, the invention may be used to detect target sequences specific to pathogens such as anthrax, hepatitis B, and *E. coli*. Probes have also been synthesized that detect for the mutation on codon 526 of the rpoB gene that leads to multi-drug resistance in *M. tuberculosis* (Arnold, *CIM*, 2004). These probes can be ligated.

Figure 10:
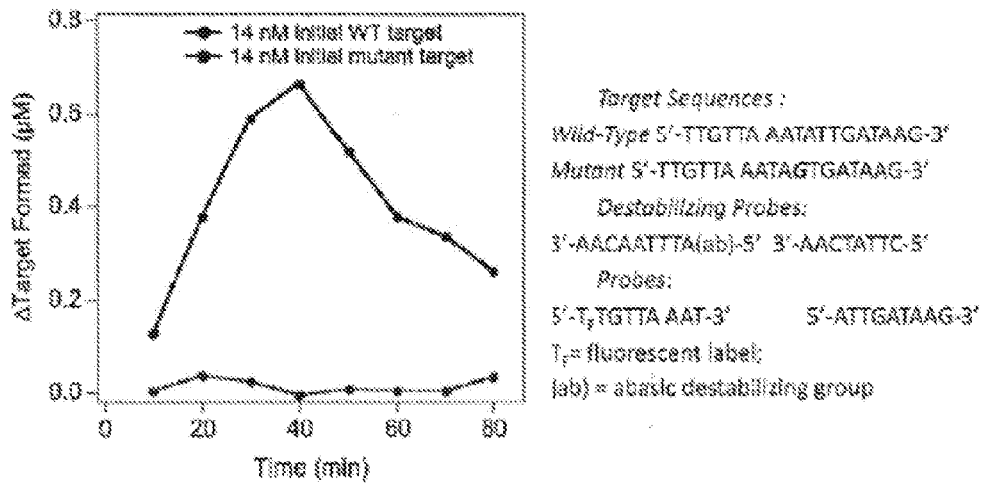
FIG. 10 is a graph showing the difference in target formed over time using the indicated sequences, including a mutant target sequence having a mutation (G instead of T) near the ligation site.

In one embodiment, the invention enables detection of single-point mutations with a high degree of discrimination (FIG. 10). Since the method is sensitive to the rate of each step in the cycle, the presence of a mutation at the ligation site (G instead of T) slows down ligation, which has a major affect on the amplification rate. Amplification is thus only slightly higher than the background reaction when a mismatch is present at the ligation site. Consequently, at specific points of the amplification process, difference ratios are seen between the mismatch and perfect target samples greater than 100, which is a very high signal ratio for mismatch detection.

The method of the present invention may occur isothermally owing to the presence of one or more destabilizing groups in the target probes. Adding mismatches to the probes can lead to enhanced destabilization and quicker amplification. Additionally, using combinations of abasic groups and mismatches, the temperature of the amplification process has been tuned from 13° C. to 30° C. As long as the mismatches are added away from the ligation site, they promote faster amplification.

Figure 11:
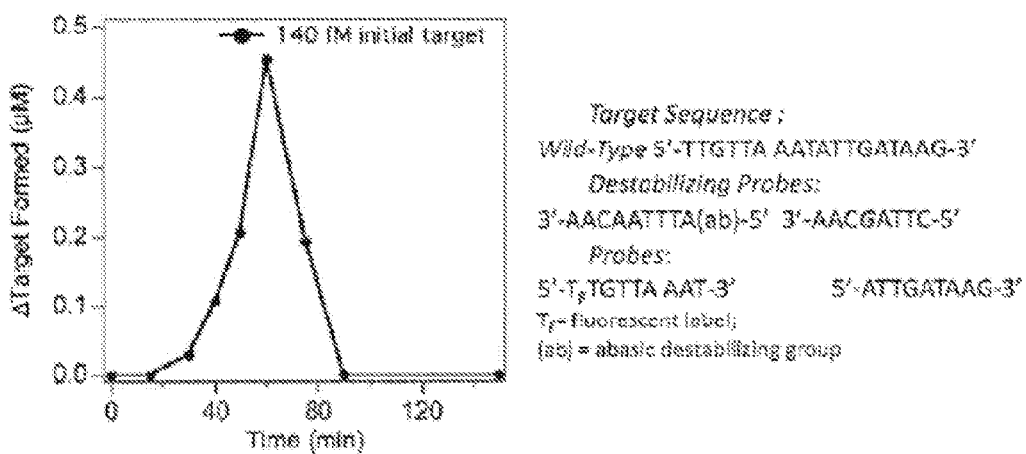
FIG. 11 is a graph showing the difference in target formed over time using the indicated sequences, including a probe containing one model abasic and a probe containing one mismatch (G instead of T, not at the ligation site).

In one embodiment, the amplification method may be optimized by varying the probe concentration and by employing probes containing one model abasic and one mismatch (G, not at the ligation site), which has a limit of detection as low as 14 pM of target. Sensitivity of the assay may be improved with a method of serial ligation. In one embodiment, the target sequence is first combined with low probe concentrations (140 nM) and enzyme (1 µL high concentration per 15 µL reaction). At these low probe concentrations, the background reaction is very slow. After 2 hours, an aliquot of this mixture is removed and added to more concentrated probes (1.4 µM) and enzyme (1 µL high concentration per 15 µL reaction). This serial ligation method improves sensitivity, detecting as low as 140 fM target DNA (FIG. 11).

The probes can form duplexes that have single base pair overhangs, which the enzyme is able to ligate quite efficiently. In order to reduce this reaction, in one embodiment, a system has been developed in which these duplexes have blunt ends, which has led to a reduction in the rate of background ligation. Additionally, T4 DNA ligase can still join blunt ends although this reaction is slow. *E. coli* ligase, an enzyme inefficient at ligating blunt ends, may eliminate the background and allow detection of even lower target concentrations.

*E. coli* has been detected using probes that are complementary to the *E coli* DNA ligase gene. This sequence can be detected on plasmid DNA containing approximately 6000 base pairs. To detect the double-stranded genomic DNA, the genomic DNA is first heated in a solution containing the probes, to 95° C. and then allowed it to cool for 20 minutes before adding the enzyme. Additionally, *E. coli* target was directly detected from cell lysate. Several colonies of *E. coli* were dispersed in 50 µL water. The solution was then heated to 95° C. to lyse the cells and inactivate any native enzymes. An aliquot of the lysate was then diluted 10-fold and added it to the probes (14 µM). The solution was then heated to 95° C. to dissociate the genomic DNA and the enzyme (5 units) was added after the solution had cooled for 20 minutes. The presence of *E. coli* was easily detected after 3 hours. To confirm that the components of the cell lysate were not influencing the replication rate as they were not present in the reference control, the same experiment was performed using the wrong probes (Hepatitis B probes) in the *E. coli* cell lysate. The amount of replication was indistinguishable from the control lacking any genomic target, which proved that replication was target-initiated for the *E. coli* experiments.

Polyacrylamide gel electrophoresis has been used to monitor the formation of the target strand during the reaction using a fluorescent label on one of the corresponding probe strands. In one embodiment, the amplification of the target sequence may be detected using real-time or chip-based methods of detecting the product. In one approach, one probe is modified with a fluorescent donor (FAM) and another probe with a fluorescent acceptor (TAMRA or Cy5). Upon ligating the probes to form a target sequence, Forster resonant energy transfer (FRET) is observed, which provides a real-time method for monitoring amplification of the target. The FRET method may be useful with standard plate readers. In another embodiment, one of the probe strands is immobilized to a surface and the other probe strand is modified with a gold nanoparticle. After templated-ligation of the two probes occurs, the gold nanoparticle is covalently attached to the surface, which can be observed by silver plating through the catalytic reduction of silver (I) onto the gold nanoparticles. Surface-based detection can be monitored using a flatbed scanner to observe the silver plating.

The applicants have demonstrated that DNA templates for enzymatic ligation reactions can turn over in the ligation cycle by introducing a destabilizing modification into the template strand. The turnover numbers are higher than isothermal chemical ligation strategies at similar strand lengths, concentrations, and ratios (Grossman et al., 2008; Silverman et al., 2006). Further, the present invention adds another cycle that leads to a self-replicating DNA system using destabilization to overcome product inhibition. The success of the abasic probes in both cycles is especially promising as this phosphoramidite is commercially available, allowing simple access to templates capable of turnover. The invention not only enables advances in nanotechnology in the replication of DNA materials, but also is useful in isothermal target amplification for the broad field of DNA diagnostics. With simple destabilizing groups and rapid ligation methods, turnover and target initiated self-replication are made possible.

Where there are discrepancies between this and the provisional patent application from which priority is claimed, this application shall dominate.

A Weiss unit as used herein is defined as the amount of enzyme needed to catalyze the transformation of 1 nmol of pyrophosphate in 0.1 mL into ATP in 20 minutes at 37° C., which is equivalent to approximately 300 cohesive end units defined as the amount of enzyme needed to catalyze the ligation of 50% of 0.12 M Hind III λ-DNA fragments in 20 µL in 30 minutes at 16° C. The enzyme concentration used in the method of the present invention can be any suitable range including, but not limited to, from about 1 to about 20 Weiss units, from about 1 to about 15 Weiss units, from about 5 to about 20 Weiss units, or from about 5 to about 15 Weiss units, for example. A Weiss unit of 15 is equivalent to approximately 4500 cohesive end units defined as the amount of enzyme needed to catalyze the ligation of 50% of 0.12 M Hind III λ-DNA fragments in 20 µL in 30 minutes at 16° C.

The target nucleic acid sequence, as described herein, may be any suitable nucleic acid sequence or portion of a target nucleic acid sequence, such as a segment of a DNA sequence. A segment of a DNA sequence may be any suitable segment length having any suitable base quantity including, but not limited to, from about 7 to about 30 bases, from about 10 to about 30, from about 15 to about 25, greater than about 10 bases, greater than about IS bases, no more than 30 bases, no more than 25 bases, no more than 20 bases, from about 13 to about 24, or any range between and including the base quantities provided. For example, an original target nucleic acid sequence segment may be a segment of a DNA sequence having 17 bases. A DNA sequence having at least 13, or more preferably at least 15, and even more preferably 17 or more bases may provide better statistical certainty of the identification of a target sequence. Any organic species is more reliable identified when a DNA sequence of at least 17 is amplified.

A target nucleic acid sequence or the original target nucleic acid sequence segment may be a DNA target sequence formed by providing a RNA sequence, providing DNA probes that are complimentary to the RNA sequence and reacting the reacting the RNA sequence with at least two DNA probes. The reaction includes the steps of hybridizing, ligating and dissociating to produce the DNA target sequence segment, which can then undergo the amplification method as described herein, such as in the amplification methods as described in steps a-g to produce a DNA target sequence segment that consists substantially of the same original target nucleic acid sequence segment.

The phrase "consists substantially of the same original target nucleic acid sequence segment", as used herein, means that the product nucleic acid sequence segment produced comprises at least 75% of the same composition as the original target nucleic acid, and may comprise a fluorescence compound or marker and may comprise linkages that are different than the target nucleic acid. In some embodiments, the nucleic acid sequence segment produced comprises at least 80%, 85%, 90%, or 95%, the same composition as the original target nucleic acid sequence. In some embodiments, the method, as described herein, produces multiple copies of a product nucleic acid sequence that consists of the same original target nucleic acid sequence segment. The phrase "consists substantially of the same original target nucleic acid sequence segment", as used herein, means that a certain percentage of the nucleobases present in the original target sequence segment are present in the target sequence segment copies. Additional functional groups, in addition to the original nucleotides, may also be present such as fluorescent labels. For example, 85% of the phosphate-sugar backbone of the original target nucleic acid sequence should be present in the product nucleic acid sequence including phosphorothioate sugar linkages. The remaining 15% may include different linkages than thiophosphate- or phosphate-sugar linkages such as acetylamido thiophosphate linkages or phosphorodithioate linkages.

In some embodiments, complementary, means that a probe is at least 75% complementary to a portion of a sequence it is hybridizing with, and may comprise destabilizing moieties that are not complementary.

The term "target probes consists substantially of a DNA sequence", as used herein, means that the target probe has a composition that is at least 85% that of a DNA sequence.

The term "template probes consists substantially of a DNA sequence", as used herein, means that the template probe has a composition that is at least 85% that of a DNA sequence.

Any suitable liquid may be used for conducting the nucleic acid amplification by the destabilization method described herein including, but not limited to, water-base solutions and buffer solutions, solutions comprising solvent or enzymes and the like. Examples of buffer solutions include, but are not limited to, 70 mM Tris-borate buffer, 10 mM $MgCl_2$, pH 7.0; and 10 mM Tris-HCl; 10 mM $MgCl_2$; 10 microM ATP, pH 7.5 at 25° C., 50 mM Tris-HCl, 10 mM $MgCl_2$, 1 mM ATP, 1 mM DTT that is pH 7.5 at 25° C. Another example of a suitable liquid is an aqueous buffer consisting of 50 mM Tris-HCl (pH 7.6), 10 mM $MgCl_2$, 1 mM ATP, 1 mM DTT, 5% (w/v) polyethylene glycol-8000. Another example of a suitable liquid is an aqueous buffer consisting of X. In one embodiment, the method is conducted in single liquid vessel whereby all components required for the method are added to a single liquid vessel. In one embodiment, a plurality of process steps occur concurrently after the destabilizing template is produce and template probes complementary to the destabilizing template are provided. After the template probes, that are complementary to the destabilizing template, are ligated together to form a product nucleic acid sequence that consists substantially of the same original target nucleic acid sequence segment, all steps of the method can occur concurrently.

The method, as described herein, may be conducted in a liquid at any suitable temperature and may be an isothermal method wherein the temperature of the liquid is substantially maintained within a temperature range throughout the entire method. For example, the temperature of a liquid in an isothermal method, as described herein, may be kept within a temperature range of about 10° C., about 8° C., about 5° C., about 3° C., or about 2° C. In some embodiments however, the temperature of the liquid may be increased during selected method steps to promote or increase the rate of dissociations. The method, as described herein, may be conducted in a liquid at any suitable temperature, including, but not limited to, from about 10° C. to about 45° C., from about 10° C. to about 30° C., from about 13° C. to about 30° C., greater than 5° C., greater than 10° C., no more than 50° C., no more than 40° C., or no more than 30° C.

A destabilizing moiety may be any suitable type or combination of types. Two or more destabilizing moieties may be used in the method, as described herein. For example, a plurality of different types of target probes that are complementary to an original target nucleic acid sequence segment having different destabilizing moieties may be used. A destabilizing moiety may be selected from the group consisting of: an abasic nucleotide, a model abasic, butyl, cis-butenyl, or ethyl group, and/or a mismatched nucleotide. In addition, destabilizing moieties may comprise, ethyl, butyl, cis-butenyl groups linked through a phosphate or a similar functional group to the 5' end or 3' end of a nucleoside. Abasic groups based on naturally occurring 1'-hydroxy2'deoxyribose-5'phosphate can also be used as destabilizing moiety. Model abasic groups such as 1',2'-dideoxyribose-5'phosphate can also be used as the destabilizing moiety.

A target nucleic acid sequence or destabilizing template may be detected using any suitable method as know and practiced by those skilled in the art, including fluorescence using a molecular beacon that is complementary to the target sequence copies; using a fluorescent molecule like Sybr-Green that changes fluorescence upon binding to double-stranded DNA, which in this case would be the product duplexes; Forster resonant energy transfer based on the presence of both a donor and acceptor fluorophore in the target sequence copy, detection using DNA-modified gold nanoparticles that are all or partially complementary to the target DNA sequence copies.

Figure 12:
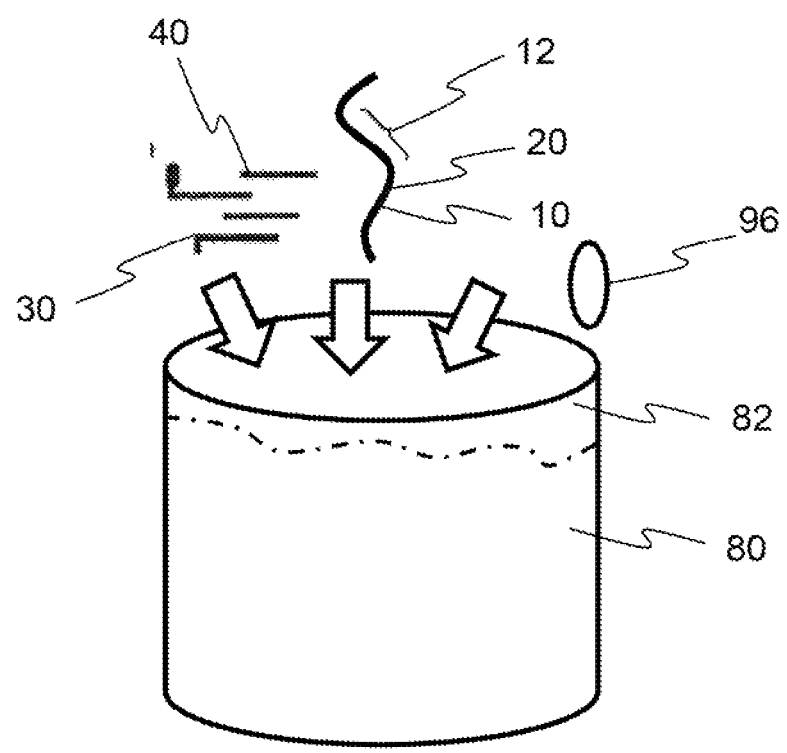
FIG. 12 shows a reaction vessel with components of the method being added into a reaction liquid.

A shown in FIG. 1 a destabilizing template 60 is being produced along with product nucleic acid sequences 16. A product duplex 50 is also shown in FIG. 1. As shown in FIG. 2, a target nucleic acid sequence 10 may comprise the original target nucleic acid sequence segment 12. The target nucleic acid sequence, which may be a segment of a much longer nucleic acid sequence, and target probes 40 may be added to a reaction vessel 82 comprising a reaction liquid 80, as shown in FIG. 2 and FIG. 12. A destabilizing probe for the target nucleic acid sequence or a target probe 40 is shown being added to the vessel 82 comprising the reaction liquid 80 in FIG. 2.

FIG. 3 shows a destabilizing template 60 having two template probes 30, 30', or fragments, as referred herein, hybridized to the destabilizing template. A variety of destabilizing moieties 70 are shown in FIG. 3, D as well.

Target probes are also referred to herein as destabilizing probes and destabilizing fragments.

Template probes are also referred to herein as probes and fragment.

The original target sequence segment is also referred to herein as the initial target.

Figure 8A:
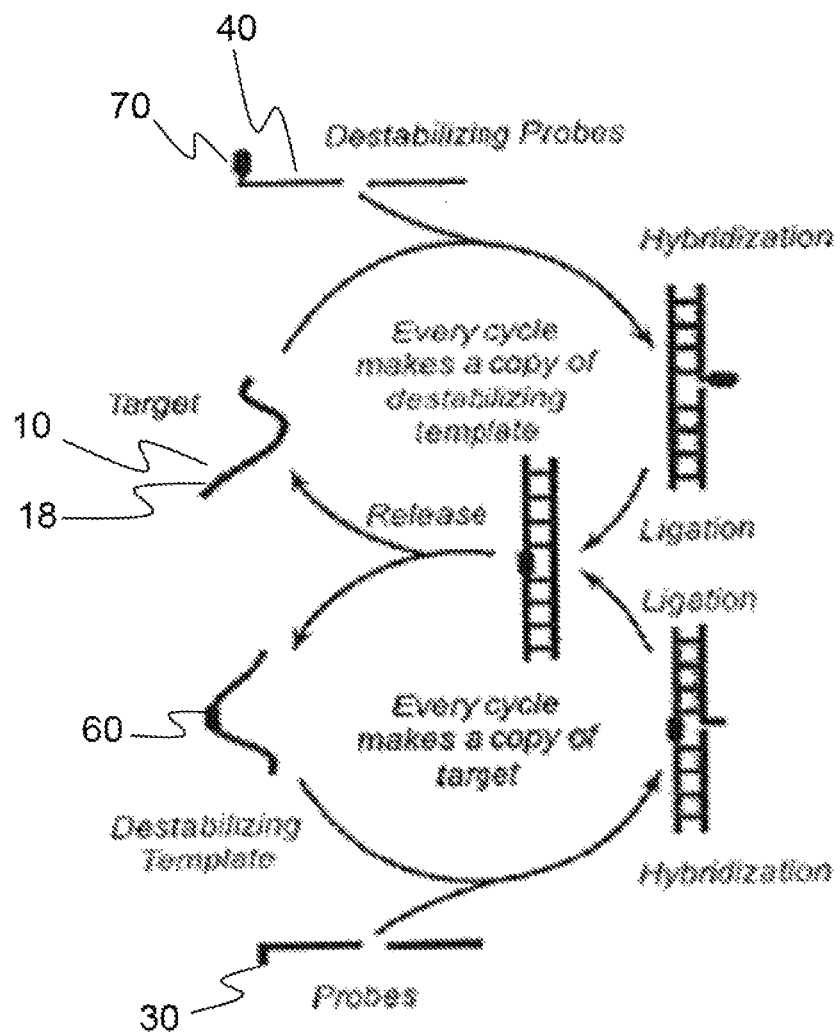
FIG. 8A is a schematic diagram showing cross catalytic cycles using destabilizing probes, preferably containing a model abasic destabilizing group.
Figure 8A:

A target nucleic acid sequence may be RNA 18 in some embodiments, as shown in FIG. 8A. FIG. 8A shows a destabilizing probe for the target 10, or a target probe 40, having a destabilizing moiety 70. An abasic type destabilizing moiety 70 is shown in FIG. 8A along with template probes 30 which in some cases may be referred to as probes herein. Also shown in FIG. 8A is a destabilizing template 60.

Figure 8B:
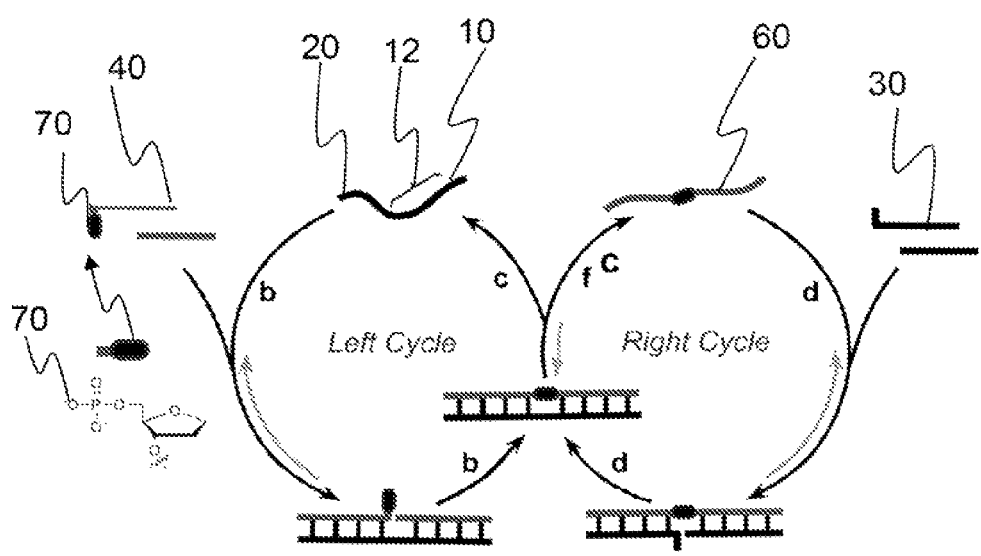
FIG. 8B is a schematic diagram showing cross catalytic cycles using destabilizing probes, preferably containing a model abasic destabilizing group.

FIG. 8B shows a target nucleic acid sequence 10 being a DNA sequence 20 having a original target nucleic acid sequence segment 12. A target probe 40 having a destabilizing moiety 70, a model abasic moiety, is shown being combined with the target nucleic acid sequence 10. On the right cycle, a destabilizing template 60 is shown with template probe 30.

FIG. 12 shows a target nucleic acid sequence 10 that is a DNA target sequence 20, having an original target nucleic acid sequence segment 12, being added along with target probes 40, template probes 30 and enzyme 96 to a reaction vessel 82. The process can occur concurrently after the first a-c cycle, as described in paragraph 81 herein, which generates the destabilizing template. Thereafter, both steps a-c and d-f are occurring simultaneously. Because these processes are concurrent, they can lead to exponential formation of the product target nucleic acid sequence with time. This exponential amplification is ideal for achieving very large amplification numbers, which allows smaller quantities of target nucleic acid sequences to be produced and/or detected.

Figure 13:
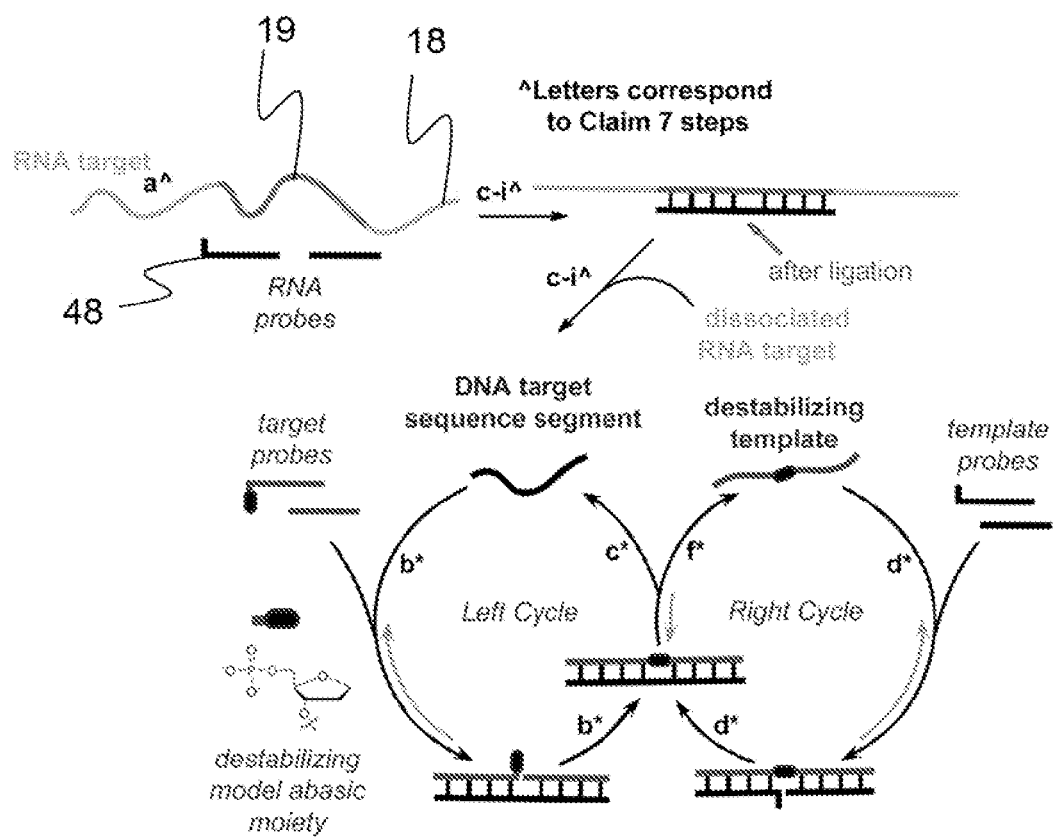
FIG. 13 shows a diagram illustrating a RNA initiated DNA amplification method.

FIG. 13 shows a diagram illustrating a RNA initiated DNA amplification method wherein the RNA probes 48 are provided that are complementary to a RNA target sequence segment 19, which can be part of a larger RNA target 18. These probes hybridize and then are ligated followed by dissociation. In one manifestation the RNA probes are comprised of DNA. Therefore, the newly formed dissociated strand represents the DNA target sequence segment that can be amplified by hybridizing with target probes that contain at least one destabilizing moiety followed by ligation of the target probes. Because of destabilization, the newly formed destabilizing template will separate, or dissociate, from the original DNA target sequence segment (c*). The left cycle will then continue repeating. Simultaneously, the released destabilizing template will hybridize with template probes that may or may not contain destabilizing groups, followed by ligation of the template probes. This results in a new strand that is substantially similar or identical to the original DNA target sequence segment. This strand and the destabilizing template dissociate (f*) and both cycles continue concurrently. As a result, one RNA target can initiate exponential amplification of DNA target sequence copies. The letters in FIG. 13 represent the following method steps:

(a) providing target probes that are complementary to an original target nucleic acid sequence segment wherein at least one target probe comprises at least one destabilizing moiety;

(b) hybridizing the target probes to the original target nucleic acid sequence segment and ligating the target probes together to form a first product duplex comprising the original target nucleic acid sequence segment and a newly generated destabilizing template;

(c) dissociating the first product duplex to release the original target nucleic acid sequence segment and the destabilizing template;

(d) providing template probes complementary to the destabilizing template that when ligated together form a product nucleic acid sequence that consists substantially of the same original target nucleic acid sequence segment;

(e) hybridizing the template probes to the destabilizing template and ligating the template probes together to form a second product duplex comprising a destabilizing template and a newly generated product nucleic acid sequence that consists substantially of the same original target nucleic acid sequence segment;

(f) dissociating the second product duplex to produce the destabilizing template and a product nucleic acid sequence that consists substantially of the same original target nucleic acid sequence; and (g) repeating steps (a) to (f) to produce multiple copies of the destabilizing template and multiple copies of a product nucleic acid sequence that consists substantially of the same original target nucleic acid sequence segment.

Exemplary embodiments of the present invention are described in the following Examples, which are set forth to aid in the understanding of the invention, and should not be construed to limit in any way the scope of the invention as defined in the claims which follow thereafter.

EXAMPLE 1

Preparation of DNA Strands

DNA was synthesized on an ABI 380 solid-phase synthesizer using Glen Research reagents. Strands were purified by Glen-Pak DNA Purification cartridges (cat. 60-5200-01) according to the DMT-On protocol. Standard nucleotide phosphoramidite and the following were used: Chemical Phosphorylation Reagent II (cat. 10-1901-90), Fluorescein-dT Phosphoramidite (cat. 10-1056-95), and dSpacer CE Phosphoramidite (cat 10-1914-90) for the abasic (Ab) template and fragments. All other destabilizing templates were prepared from the corresponding protected diols with solid-phase synthesis. OligoCalc (http://www.basic.northwestern.edu/biotools/oligocalc.html) was used to determine the extinction coefficients where the destabilizing templates' absorptivity was assumed to be Ac, with D=a deletion.

TABLE 1

| DNA Strands | |
|---|---|
| Strands | |
| Ac | 3'-AACAATTTA-D-AACTATTC-5'; |
|  | D = T or destabilizing group |
| A | 3'-GAATAGTT-A-TAAATTGTT-5' |
| C | 3'-GAATAGTTA-5' |
| $C_P$ | 3'-GAATAGTTA$_{Phosphate}$-5' |
| B | 3'-TAAATTGTT-5' |
| $B_F$ | 3'-TAAATTGTT$_{Fluorescein}$-5' |
| Cc | 3'-AACTATTC-5' |
| $Bc_P$ | 3'-AACAATTTAT$_{Phosphate}$-5' |
| $BcAb_P$ | 3'-AACAATTTA(Ab)$_{Phosphate}$-5' |

EXAMPLE 2

Thermal Dissociation Experiments 1.3 nmol of each DNA sequence (Ac and A for the product duplex experiments and Ac, B, and C for the nicked duplex experiments) was combined in PBS buffer (1.0 mL, 10 mM MgCl$_2$, 20 mM pBS, pH 7.0) and allowed to hybridize for about 15 min. While stirring at 100 rpm, absorbance readings at 260 nm were taken from 10 to 60° C. at 1° C. intervals, with 1 min hold time.

EXAMPLE 3

Ligation Experiments

Strand amounts were for single cycle reactions were: B$_F$, 1 equiv; C$_P$, 2 equiv; and 1 or 0.01 equiv of template (Ac); and for cross cycle reactions were: B$_F$, 1 equiv; C$_P$, 2 equiv; A, 0.01 or 0.001 equiv; Cc, 2 equiv; and either strand Bc$_P$ or BcAb$_P$, 2 equiv. In a typical ligation, where 1 equiv=21 pmol, the appropriate amounts of DNA fragments and template were first combined in water in a 400-µL mini-centrifuge tube to reach a final volume of 10 µL and incubated at the desired reaction temperature. While several of these DNA solutions incubated, in a separate mini-centrifuge tube, T4 DNA ligase (8 µL) at lower concentration (1 Unit/µL, Invitrogen cat. 15224-017) or higher concentration (5 Units/µL, Invitrogen cat. 46300-018) was mixed with ligation buffer (24 µL, 5× concentrated) and water (8 µL). A portion of this ligase mixture (5 µL) was immediately added to each of the DNA solutions (final [DNA]=1.4 µM for each equivalent). The reactions were then placed in a covered thermal incubator for 20 hours unless otherwise noted. To stop ligation, EDTA$_{(aq)}$ (1 µL, 0.5 M) was added for every unit of enzyme present. For the kinetic experiments, aliquots (3 µL) were removed from the bulk ligation mixture at various reaction times and placed in a separate microcentrifuge tube containing EDTA$_{aq}$ (1 µL, 0.5 M). Samples were stored at 4° C. until analyzed by 15% denaturing PAGE.

REFERENCES

The following references are incorporated herein by reference (where permitted) as if reproduced in their entirety. All references are indicative of the level of skill of those skilled in the art to which this invention pertains.

Abe, H.; Kool, E. T. *J. Am. Chem. Soc.* 2004, 126, 13980-13986.
Albagli, D.; Atta, R. V.; Cheng, P.; Huan, B.; Wood, M. L. *J. Am. Chem. Soc.* 1999, 121, 6954-6955.
Aldaye, F. A.; Palmer, A. L.; Sleiman, H. F. *Science* 2008, 321, 1795-1799.
Alexander, R. C.; Johnson, A. K.; Thorpe, J. A.; Gevedon, T.; Testa, S. M. *Nucleic Acids Res.* 2003, 31, 3208-3216.
Claridge, S. A.; Mastroianni, A. J.; Au, Y. B.; Liang. H. W.; Micheel, C. M.; Frechet, J. M. J.; Alivisatos, A. P. *J. Am. Chem. Soc.* 2008, 130, 9598-9605.
Connolly, A. R.; Trau, M. *Angew Chem. Int. Ed.* 2010, 49, 2720-2723.
Dose, C.; Ficht, S.; Seitz, O. *Angew. Chem. Int. Ed.* 2006, 45, 5369-5373.
Ficht, S.; Dose, C.; Seitz, O. *ChemBioChem* 2005, 6, 2098-2103.
Grossmann, T. N.; Strohbach, A.; Seitz, O. *ChemBioChem* 2008, 9, 2185-2192.
Gu, H.; Chao, J.; Xiao, S.-J.; Seeman, N. C. *Nature* 2010, 465, 202-205.
Li, X.; Chmielewski, J. *J. Am. Chem. Soc.* 2003, 125, 11820-11821.
Lincoln, T. A.; Joyce, G. F. *Science* 2009, 323, 1229.
Lund, K.; Manzo, A. J.; Dabby, N.; Michelotti, N.; Johnson-Buck, A.; Nangreave, J.; Taylor, S.; Pei, R.; Stojanovic. M. N.: Walter, N. G.; Winfree, E.; Yan, H. *Nature* 2010, 465, 206-210.
Mammen, M.; Choi, S.-K.; Whitesides, G. M. *Angew. Chem. Int. Ed.* 1998, 37, 2754-2794.
Matray, T. J.; Kool. E. T. *J. Am. Chem. Soc.* 1998, 120, 6191-6192.
Mendel-Hartvig, M.; Kumar, A.; Landegren, U. *Nucleic Acids Res.* 2004, 32, e2.
Orgel, L. E. *Nature* 1992, 358, 203-209
Patzke, V.; von Kiedrowski, G. *ARKIVOC* 2007, 293-310.
Paul, N.; Joyce, G. F. *Curr Opin. Chem. Biol.* 2004, 8, 634-639.
Sando, S.; Abe, H.; Kool, E. T. *J. Am. Chem. Soc.* 2004, 126, 1081-1087.
Silverman, A. P.; Kool, E. T. *Chem. Rev.* 2006, 106, 3775-3789.
Verly, C. G. a. W. G. *Nucleic Acids Res.* 1983, 11, 8103-8109.
Xue, X.; Zu, W.; Wang, F.; Liu, X. *J. Am. Chem. Soc.* 2009, 131, 11668-11669.
Ye, J.; Gat, Y.; Lynn, D. G. *Angew. Chem. Int. Ed.* 2000, 39, 3641-3643.
Zhan, Z.-Y. J.; Lynn, D. G. *J. Am. Chem. Soc.* 1997, 119, 12420-12421.
Zielinski, W. S.; Orgel, L. E. *Nature* 1987, 327, 346-347.

What is claimed is:

1. A method for amplifying a target nucleic acid sequence comprising the steps of:
   (a) providing target probes, having a first end and a second end, that are complementary to an original target nucleic acid sequence segment wherein at least one target probe comprises at least one destabilizing moiety that is located at or near the first end that is to be ligated of the target probe;
   (b) hybridizing the target probes to the original target nucleic acid sequence segment and ligating the target probes together to form a first product duplex comprising the original target nucleic acid sequence segment and a newly generated destabilizing template;
   wherein said at least one destabilizing moiety that was located at or near the first end of the target probe in step (a) is located near a middle of the destabilizing template;
   (c) dissociating the first product duplex spontaneously as a result of a destabilizing effect of the destabilizing moiety to release the original target nucleic acid sequence segment and the destabilizing template;
   (d) providing template probes complementary to the destabilizing template that when ligated together form a product nucleic acid sequence that consists substantially of the same original target nucleic acid sequence segment;
   (e) hybridizing the template probes to the destabilizing template and ligating the template probes together to form a second product duplex comprising a destabilizing template and a newly generated product nucleic acid sequence that consists substantially of the same original target nucleic acid sequence segment;
   (f) dissociating the second product duplex spontaneously as a result of a destabilizing effect of the destabilizing moiety to produce the destabilizing template and a product nucleic acid sequence that consists substantially of the same original target nucleic acid sequence; and
   (g) repeating steps (a) to (f) to produce multiple copies of the destabilizing template and multiple copies of a product nucleic acid sequence that consists substantially of the same original target nucleic acid sequence segment,
   wherein the destabilizing moiety is selected from the group consisting of: an abasic nucleotide, a 1',2'-dideoxyribose-5'-phosphate, butyl, cis-butenyl, or ethyl group;
   wherein the method is an isothermal method and the temperature of the liquid is maintained within a temperature range of about 5° C.;
   wherein the method for amplifying a target nucleic acid sequence is conducted in a liquid.

2. The method of claim 1, wherein the product nucleic acid sequence has a composition that is at least 90% the same as original target nucleic acid sequence segment.

3. The method of claim 1, wherein the product nucleic acid sequence has a base quantity of between about 13 and 24 bases.

4. The method of claim 1, wherein steps a-g occur concurrently in a single liquid vessel.

5. The method of claim 1, wherein the target nucleic acid sequence is a DNA sequence.

6. The method of claim 1, wherein the target nucleic acid sequence is a RNA sequence.

7. The method of claim 1, wherein the target probes consists substantially of a DNA sequence.

8. The method of claim 1, wherein the template probes consists substantially of a DNA sequence.

9. The method of claim 1, wherein the target probe consists substantially of a DNA sequence and the template probes consists substantially of a DNA sequence.

10. The method of claim 1, wherein the original target nucleic acid sequence segment in step A of claim 1 is a DNA target sequence formed by the method comprising the steps of:
   a) providing a RNA sequence;
   b) providing DNA probes complementary to the RNA sequence; and
   c) reacting the RNA sequence with at least two DNA probes comprising the steps of:
      i) hybridizing, ligating and dissociating;
   to produce the DNA target sequence segment, which can then undergo steps 1a-g.

11. A method for amplifying a target nucleic acid sequence comprising the steps of:
   (a) providing target probes that are complementary to an original target nucleic acid sequence segment wherein at least one target probe comprises at least one destabilizing moiety that is located at or near the first end that is to be ligated of the target probe;
   (b) hybridizing the target probes to the original target nucleic acid sequence segment and ligating the target probes together to form a first product duplex comprising the original target nucleic acid sequence segment and a newly generated destabilizing template;
   (c) dissociating the first product duplex spontaneously as a result of a destabilizing effect of the destabilizing moiety to release the original target nucleic acid sequence segment and the destabilizing template;
   (d) providing template probes complementary to the destabilizing template that when ligated together form a product nucleic acid sequence that consists substantially of the same original target nucleic acid sequence segment;
   (e) hybridizing the template probes to the destabilizing template and ligating the template probes together to form a second product duplex comprising a destabilizing template and a newly generated product nucleic acid sequence that consists substantially of the same original target nucleic acid sequence segment;
   (f) dissociating the second product duplex spontaneously as a result of a destabilizing effect of the destabilizing moiety to produce the destabilizing template and a product nucleic acid sequence that consists substantially of the same original target nucleic acid sequence; and
   (g) repeating steps (a) to (f) to produce multiple copies of the destabilizing template and multiple copies of a product nucleic acid sequence that consists substantially of the same original target nucleic acid sequence segment,
wherein the destabilizing moiety comprises an 1',2'-dideoxyribose-5'-phosphate;
wherein the method is an isothermal method and the temperature of the liquid is maintained within a temperature range of about 5° C.; and
wherein the method for amplifying a target nucleic acid sequence is conducted in a liquid.

12. The method of claim 1, wherein at least one of the probes comprise one or more mismatches not at a ligation site.

13. The method of claim 1, comprising the further step of detecting the target sequence or the destabilizing template.

14. The method of claim 13, wherein the step of detecting comprises the discrimination between a perfect target sequence and a sequence with a single base pair mismatch.

15. The method of claim 13, wherein the detection step comprises the steps of separately labeling the probes with a fluorescent donor and a fluorescent acceptor, and detecting Forster resonant energy transfer after ligation.

16. The method of claim 13, wherein the step of detecting comprises the steps of:
   immobilizing a probe to a glass surface while another probe in solution is labeled with a gold nanoparticle,
   covalently binding said gold nanoparticle to the surface following ligation of the two probes, and
   detecting the gold nanoparticle by catalytic silver reduction plating.

17. The method of claim 1, wherein the target probes and template probes each have a concentration within a concentration range of about 140 nM to about 1.4 µM.

18. The method of claim 1, comprising a first ligation stage and a second ligation stage, wherein the first ligation stage comprises steps (a)-(f) at a first target probe and a first template probe concentrations and the second ligation stage follows the first ligation stage and comprises steps (a)-(f) at a second target probe and a second template probe concentrations that are at least two times higher than the first target probe and the first template probe concentrations.

19. The method of claim 18, wherein the second target or second template probe concentration is about 10 times higher than the first target or first template probe concentration respectively.

20. The method of claim 1, wherein the liquid is kept within a temperature ranging between about 13° C. to about 30° C. throughout the method.

21. The method of claim 1, wherein the liquid comprises an enzyme that ligates the template probes and/or target probes.

22. The method of claim 21, wherein the enzyme comprises a T4 DNA Ligase.

23. The method of claim 21, wherein the enzyme has a concentration range from about 1 to about 5 Weiss units.

24. The method of claim 1, wherein the multiple copies of a product nucleic acid sequence consists of the same original target nucleic acid sequence segment.

25. A method for amplifying a target nucleic acid sequence comprising the steps of:
   (a) providing target probes, having a first and a second end, that are complementary to an original target nucleic acid sequence segment wherein at least one target probe comprises at least one destabilizing moiety that is located at or near the first end of the target probe;
   (b) hybridizing the target probes to the original target nucleic acid sequence segment and ligating the target probes together to form a first product duplex comprising the original target nucleic acid sequence segment and a newly generated destabilizing template; wherein said at least one destabilizing moiety that was located at or near the first end of the target probe in step (a) is located near the middle of the destabilizing template;

(c) dissociating the first product duplex spontaneously as a result of a destabilizing effect of the destabilizing moiety to release the original target nucleic acid sequence segment and the destabilizing template;

(d) providing template probes complementary to the destabilizing template that when ligated together form a product nucleic acid sequence that consists substantially of the same original target nucleic acid sequence segment;

(e) hybridizing the template probes to the destabilizing template and ligating the template probes together to form a second product duplex comprising a destabilizing template and a newly generated product nucleic acid sequence that consists substantially of the same original target nucleic acid sequence segment;

(f) dissociating the second product duplex spontaneously as a result of a destabilizing effect of the destabilizing moiety to produce the destabilizing template and a product nucleic acid sequence that consists substantially of the same original target nucleic acid sequence; and (g) repeating steps (a) to (f) to produce multiple copies of the destabilizing template and multiple copies of a product nucleic acid sequence that consists substantially of the same original target nucleic acid sequence segment, wherein the method for amplifying a target nucleic acid sequence is conducted in a single liquid vessel, wherein the liquid is kept within a temperature between about 13' C to about 30° C. throughout the method, wherein the product nucleic acid sequence has a base quantity of between about 13 and 24 bases, wherein the target probe consists substantially of a DNA sequence and the template probes consists substantially of a DNA sequence, and wherein the destabilizing moiety is selected from the group consisting of: an abasic nucleotide, a 1',2'-dideoxyribose-5'-phosphate, butyl, cis-butenyl, or ethyl group; and wherein said method is an isothermal method and the temperature of the liquid is maintained with a temperature range of about 5° C.

* * * * *

SEQUENCE LISTING

```
<160> NUMBER OF SEQ ID NOS: 19

<210> SEQ ID NO 1
<211> LENGTH: 18
<212> TYPE: DNA
<213> ORGANISM: Bacillus anthracis

<400> SEQUENCE: 1
ttgttaaata ttgataag                                                 18

<210> SEQ ID NO 2
<211> LENGTH: 9
<212> TYPE: DNA
<213> ORGANISM: Artificial Sequence
<220> FEATURE:
<223> OTHER INFORMATION: synthesized
<220> FEATURE:
<221> NAME/KEY: misc_feature
```

```
<223> OTHER INFORMATION: n=fluorescein labeled dT nucleotide
<220> FEATURE:
<221> NAME/KEY: misc_feature
<222> LOCATION: (1)..(1)
<223> OTHER INFORMATION: n is a, c, g, or t

<400> SEQUENCE: 2 ntgttaaat                                                                  9

<210> SEQ ID NO 3
<211> LENGTH: 9
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: n=5' phosphate dA nucleotide
<220> FEATURE:
<221> NAME/KEY: misc_feature
<222> LOCATION: (1)..(1)
<223> OTHER INFORMATION: n is a, c, g, or t

<400> SEQUENCE: 3 nttgataag                                                                  9

<210> SEQ ID NO 4
<211> LENGTH: 18
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: n=1', 2' dideoxyribose-5'-phosphate
<220> FEATURE:
<221> NAME/KEY: misc_feature
<222> LOCATION: (9)..(9)
<223> OTHER INFORMATION: n is a, c, g, or t

<400> SEQUENCE: 4
cttatcaana tttaacaa                                                       18

<210> SEQ ID NO 5
<211> LENGTH: 10
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: n=1', 2'-dideoxyribose-5'-phosphate
<220> FEATURE:
<221> NAME/KEY: misc_feature
<222> LOCATION: (1)..(1)
<223> OTHER INFORMATION: n is a, c, g, or t

<400> SEQUENCE: 5 natttaacaa                                                                10

<210> SEQ ID NO 6
<211> LENGTH: 8
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: n=fluorescein labeled dC nucletide
<220> FEATURE:
<221> NAME/KEY: misc_feature
```

```
<222> LOCATION: (1)..(1)
<223> OTHER INFORMATION: n is a, c, g, or t

<400> SEQUENCE: 6 nttatcaa                                                                    8

<210> SEQ ID NO 7
<211> LENGTH: 18
<212> TYPE: DNA
<213> ORGANISM: Hepatitis B virus

<400> SEQUENCE: 7
tatggatgat gtggtatt                                                        18

<210> SEQ ID NO 8
<211> LENGTH: 9
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: n=fluorescein labeled dT nucleotide
<220> FEATURE:
<221> NAME/KEY: misc_feature
<222> LOCATION: (1)..(1)
<223> OTHER INFORMATION: n is a, c, g, or t

<400> SEQUENCE: 8 natggatga                                                                   9

<210> SEQ ID NO 9
<211> LENGTH: 9
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: n=5' phosphate dT nucleotide
<220> FEATURE:
<221> NAME/KEY: misc_feature
<222> LOCATION: (1)..(1)
<223> OTHER INFORMATION: n is a, c, g, or t

<400> SEQUENCE: 9 ngtggtatt                                                                   9

<210> SEQ ID NO 10
<211> LENGTH: 18
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: n=1', 2'-dideoxyribose-5'-phosphate
<220> FEATURE:
<221> NAME/KEY: misc_feature
<222> LOCATION: (9)..(9)
<223> OTHER INFORMATION: n is a, c, g, or t

<400> SEQUENCE: 10
aataccacnt catccata                                                        18

<210> SEQ ID NO 11
<211> LENGTH: 10
<212> TYPE: DNA
<213> ORGANISM: Artificial Sequence
```

```
<220> FEATURE:
<223> OTHER INFORMATION: synthesized
<220> FEATURE:
<221> NAME/KEY: misc_feature
<223> OTHER INFORMATION: n=1', 2'-dideoxyribose-5'-phosphate
<220> FEATURE:
<221> NAME/KEY: misc_feature
<222> LOCATION: (1)..(1)
<223> OTHER INFORMATION: n is a, c, g, or t

<400> SEQUENCE: 11 ntcatccata                                                          10

<210> SEQ ID NO 12
<211> LENGTH: 8
<212> TYPE: DNA
<213> ORGANISM: Hepatitis B virus

<400> SEQUENCE: 12 aataccac                                                             8

<210> SEQ ID NO 13
<211> LENGTH: 18
<212> TYPE: DNA
<213> ORGANISM: Escherichia coli

<400> SEQUENCE: 13
atggaatcaa tcgaacaa                                                 18

<210> SEQ ID NO 14
<211> LENGTH: 9
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: n=fluorescein labeled dA nucleotide
<220> FEATURE:
<221> NAME/KEY: misc_feature
<222> LOCATION: (1)..(1)
<223> OTHER INFORMATION: n is a, c, g, or t

<400> SEQUENCE: 14 ntggaatca                                                            9

<210> SEQ ID NO 15
<211> LENGTH: 18
<212> TYPE: DNA
<213> ORGANISM: Artificial Sequence
<220> FEATURE:
<223> OTHER INFORMATION: n=1' 2'-dideoxyribose-5'-phosphate
<220> FEATURE:
<221> NAME/KEY: misc_feature
<222> LOCATION: (9)..(9)
<223> OTHER INFORMATION: n is a, c, g, or t

<400> SEQUENCE: 15
ttgttcgant gattccat                                                 18

<210> SEQ ID NO 16
<211> LENGTH: 10
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: n=1', 2'-dideoxyribose-5'-phosphate
```

```
<220> FEATURE:
<221> NAME/KEY: misc_feature
<222> LOCATION: (1)..(1)
<223> OTHER INFORMATION: n is a, c, g, or t

<400> SEQUENCE: 16 ntgattccat                                                              10

<210> SEQ ID NO 17
<211> LENGTH: 8
<212> TYPE: DNA
<213> ORGANISM: Escherichia coli

<400> SEQUENCE: 17 ttgttcga                                                                8

<210> SEQ ID NO 18
<211> LENGTH: 9
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: n=5' phosphate dA nucleotide
<220> FEATURE:
<221> NAME/KEY: misc_feature
<222> LOCATION: (1)..(1)
<223> OTHER INFORMATION: n is a, c, g, or t

<400> SEQUENCE: 18 ntcgaacaa                                                               9

<210> SEQ ID NO 19
<211> LENGTH: 18
<212> TYPE: RNA
<213> ORGANISM: Escherichia coli

<400> SEQUENCE: 19
uuguucgauu gauuccau                                                     18
```